United States Patent [19]

Somekh

[11] Patent Number: 4,482,768

[45] Date of Patent: Nov. 13, 1984

[54] SEPARATION OF ALKANOLS FROM AQUEOUS REACTION SOLUTIONS

[75] Inventor: George S. Somekh, New Rochelle, N.Y.

[73] Assignee: Union Carbide Corporation, Danbury, Conn.

[21] Appl. No.: 480,702

[22] Filed: Mar. 31, 1983

[51] Int. Cl.³ .................... C07C 29/80; C07C 29/86; C07C 29/76

[52] U.S. Cl. .................. 568/918; 568/913; 568/916; 568/917

[58] Field of Search .......................... 568/918

[56] References Cited

U.S. PATENT DOCUMENTS

| | | | |
|---|---|---|---|
| 2,050,235 | 2/1931 | Othmer | 260/122 |
| 2,354,897 | 8/1940 | Wentworth | 202/161 |
| 2,400,370 | 11/1943 | Placek | 202/42 |
| 2,506,473 | 5/1950 | Steinberger | 568/918 |
| 2,542,752 | 5/1942 | Cole | 202/60 |
| 2,582,214 | 3/1947 | Twigg | 202/60 |
| 2,597,009 | 5/1948 | Lobo et al. | 260/450 |
| 2,695,867 | 1/1950 | Chambers | 202/42 |
| 3,052,731 | 8/1959 | Murphy | 260/643 |
| 3,455,664 | 7/1969 | Rosscup et al. | 568/918 |
| 3,492,365 | 5/1966 | Anderson et al. | 260/674 |
| 3,639,497 | 8/1968 | Martel et al. | 260/674 SE |
| 3,707,575 | 8/1970 | Muller et al. | 260/666 A |
| 3,838,183 | 9/1974 | Wehrli | 568/918 |
| 4,210,495 | 4/1980 | Pinto | 203/22 |
| 4,251,231 | 2/1981 | Baird | 568/918 |
| 4,260,836 | 4/1981 | Levy | 568/918 |
| 4,399,000 | 8/1983 | Tedder | 568/918 |
| 4,403,999 | 9/1983 | Bezman | 568/918 |
| 4,425,137 | 1/1984 | Roth | 568/918 |

FOREIGN PATENT DOCUMENTS 38668 10/1981 European Pat. Off. .......... 568/918

OTHER PUBLICATIONS

Roddy, "Ind. Eng. Chem. Process Des. Div., vol. 20, No. 1, 1981, pp. 104-108.

Primary Examiner—J. E. Evans
Attorney, Agent, or Firm—Bernard F. Crowe

[57] ABSTRACT

Purified isopropanol is obtained from a crude reaction mixture by removing high boiling oils with activated carbon, extraction with a high boiling solvent and distillation with energy saving use of distillation vapors to heat successive distillation steps. Recyle of components also improves the overall economics of the process.

14 Claims, 1 Drawing Figure

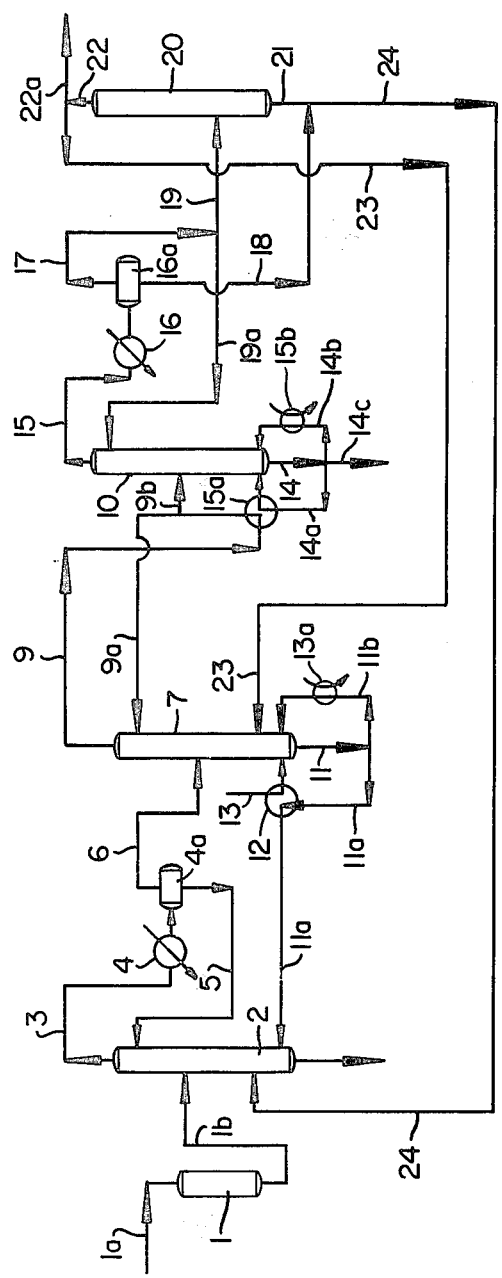

SEPARATION OF ALKANOLS FROM AQUEOUS REACTION SOLUTIONS

DESCRIPTION

1. Background of the Invention

This invention pertains to the recovery of purified alkanols from crude reaction solutions and more particularly to a series of treatment steps to achieve this end.

2. Background Art

It is known to use nonpolar solvents to extract alcohols from aqueous solutions. It is also known to employ di-alkyl ethers as entraining agents to dry alcohols. However, it is impossible to generalize about separation processes. This is due to the fact that there are major differences in the physical and thermodynamic properties of different organic compounds—even within one homologous series. For example, methanol is completely miscible and nonazeotropic with water while ethanol and the propanols are completely miscible with water and form homogeneous azeotropes with it. Five-carbon aliphatic alcohols are only partially miscible with water and form heteroazeotropes with water. Therefore, each system of alcohols must be viewed as being distinct from others.

Furthermore, one cannot as a rule take a scheme that works for one system of components and apply it to another.

With the advent of the energy crisis and the resulting high costs for energy, there has been increasing interest in the discovery of methods and processes to improve energy efficiency in the synthesis of petrochemicals. The separation steps involved in such procedures are usually energy intensive distillations. Considerable progress has been made in recent years in reducing energy requirements of such distillations. Improvements have been made by numerous techniques, i.e., by optimizing the tray count, choosing a more efficient entraining agent (for azeotropic distillations) or solvent (for extractive distillations), employing heat integration (using the vapors of one column as a heat source for another column) and the like. However, in many cases little more can be done, because such improvements as can be made have already been made.

In the instant case, the object was to find an improved process for separating and isolating alkanols having 2 to 4 carbon atoms from a mixture of impurities accompanying their syntheses and present with them in the reaction solution.

For example, it is difficult to extract isopropanol with a water content much below that in the azeotrope which contains 12 weight percent water (i.e., isopropanol purities above 88 weight percent). This is especially true at temperatures above 100° C. Solvents having such high selectivities tend to be limited to high molecular weight aliphatic hydrocarbons. However, such solvents also have low capacity to extract isopropanol.

Other objects will become apparent to those skilled in the art upon a further reading of the specification.

SUMMARY OF THE INVENTION

A process for separating $C_2$ to $C_4$ alkanols from an aqueous reaction solutions containing low-boiling and high-boiling oils has now been found for one such solution which comprises the steps of:

(A) Contacting said aqueous solution with activated carbon whereby the high boiling oils are removed;

(B) Extracting the aqueous solution from (A) at about 75°–250° C. with at least one high boiling organic solvent selected from the group consisting of paraffins, naphthenes, alkylated arenes, dialkylethers and aliphatic alcohols having 12 to 25 carbons;

(C) Cooling the extract from (B) whereby an alkanol-water layer and a second extract layer are obtained and recycling said alkanol-water layer back to step (B).

(D) Distilling the second or extract layer from (C) with an entraining agent, selected from the group consisting of paraffins, naphthenes and dialkyl ethers all having about 4 to 12 carbons, under superatmospheric pressure whereby a condensed vapor distillate comprising a mixture of alkanol, entraining agent and water is obtained;

(E) Distilling the distillate of (D) under atmospheric pressure employing the vapor in step (D) as a heat source into a purified alkanol bottoms product and a second distillate comprising a water-alkanol layer and an entraining agent layer;

(F) Returning part of the entraining agent from (E) to the distillation system of (E) and water washing the rest of the entraining agent to obtain:

(1) a stream of entraining agent substantially free of alkanol, and
(2) an aqueous alkanol solution; and (G) Recycling the aqueous alkanol solution from steps (E) and (F) to the extracting step (B).

The alkanols of this invention include ethanol, isopropanol, n-propanol, n-butanol, 2-methyl-2-propanol, isobutanol, and 2-butanol. The preferred alkanol is isopropanol.

DESCRIPTION OF THE INVENTION

The FIGURE is a flow plan depicting the separation of isopropanol from an aqueous solution reaction.

In the FIGURE a crude solution (stream 1a) comprising about 53 weight percent of isopropyl alcohol, 43.6 weight percent of water, 3.4 weight percent of diisopropyl ether and traces of unknown oils, is introduced into container 1 filled with activated carbon. The treated mixture then passes as stream 1b into multi-stage counter-current extractor 2 where it is extracted with hexadecane solvent entering 2 as stream 11a.

The extract from 2, stream 3, is cooled in heat exchanger 4 and decanted in decanter 4a. Much of the water is oiled out.

The aqueous layer from 4a is recycled to extractor 2 as stream 5. The second extract layer solution from 4a is passed as stream 6 at about 25° C. to a first distillation stripping column 7 operated under pressure. Diisopropyl ether, stream 23 is added to column 7 as a stripping medium.

The solvent bottoms (hexadecane and diisopropyl ether) emerging from column 7 as stream 11 is split into streams 11a and 11b. 11a is cooled by giving up much of its heat to interheater 12 used to heat column 7 through stream 13 (a liquid from the first tray of column 7) and then recycled as stream 11a to extractor 2. Column 7 is also heated by an auxiliary reboiler 13a which recirculates stream 11b to column 7.

An isopropyl alcohol-diisopropyl ether-water mixture is removed as distillate stream 9 from column 7. Stream 9 is condensed in reboiler 15a. Part of the condensate is returned to the top of column 7 as reflux stream 9a. The remainder of the condensate or stream 9b is passed to a second distillation column 10 operated at substantially atmospheric pressure. Purified isopropyl alcohol stream 14 is obtained as a bottoms product from column 10. Some purified isopropyl alcohol is withdrawn as product, 14c, some becomes stream 14a and is recycled to column 10 through reboiler 15a and the remainder becomes stream 14b which is recycled through auxiliary heater 15b back to column 10. Heater 15b need not be employed when producing wet isopropanol (2 to 4% water).

The distillate from column 10, stream 15, is condensed and separated into diisopropyl ether and water layers 17 and 18 respectively in condenser 16 and decanter 16a.

Part of diisopropyl ether layer 17 is passed as stream 19 to multi-stage counter-current extractor 20 where it is water washed to recover aqueous isopropyl alcohol therefrom as stream 21.

Part of stream 19 is removed from extractor 20 as stream 22, isopropyl ether essentially free of isopropyl alcohol, and part of stream 17 is returned as stream 19a to column 10 near the top as reflux.

Part of stream 22 is recycled as stream 23 to the base of column 7 and the remainder is discarded as stream 22a.

Water layer 18 from decanter 16a and the aqueous isopropyl alcohol stream 21 from extractor 20 are recycled back to extraction column 2 as stream 24.

The oil-saturated bed of activated carbon in container 1 is treated to remove part or all of the oils by washing out with pure, dry isopropyl alcohol. The isopropyl alcohol solution is then distilled to recover the isopropyl alcohol for reuse in treating the activated carbon in container 1 when it becomes oil saturated.

CONDITIONS FOR TREATING $C_2$-$C_4$ Alcohols.

The extraction temperature used in column 2 can be in the range of about 75°-250° C. However, a range of about 100°-150° C. is preferred. Although hexadecane is preferred for the extraction in column 2, any paraffins, naphthenes, alkylated arenes, dialkyl ethers and aliphatic alcohols having about 12 to about 25 carbon atoms can be used as the main solvent component. It is preferred to employ a minor amount of entraining agent in conjunction with the main solvent component. The entraining agent can be a paraffin, napthene or dialkyl ether or mixtures thereof ranging from about 2 to 15 weight percent and preferably from about 4 to 8 weight percent.

The solvent: feed ratio can range from about 0.5:1 to about 8:1 by weight. However, the preferred range is about 1.5:1 to about 6:1 by weight.

The extraction column 2 contains about 5 to 15 theoretical stages.

The heat exchanger 4 is preferably operated at as low a temperature as possible. However, using cooling water the lowest temperatures practical are in the range of about 20°-45° C.

Stripping column 7 is operated at a pressure of about 50 to about 100 psig. The maximum pressure is chosen so that the bottoms temperature is no more than about 250° C., to prevent excessive thermal decomposition of the hydrocarbon solvent. The minimum pressure is used to ensure that the head temperature is adequately high to be a heat source for the second distillation column 10. The reflux ratio for stripping column 7 is in the range of about 0.1:1 to about 0.4:1, with a range of about 0.1:1 to 0.25:1 being preferred. Column 7 can have about 20 to about 30 theoretical stages.

It is essential to the energy efficiency of the process that heat be recovered from the solvent leaving the bottom of stripping column 7. This heat recovery step is best accomplished by the use of an interheater 12 for column 7. The interheater 12 is located within a few theoretical stages of the reboiler supplying heat at the bottom. The amount of heat added to the interheater 12 is about equal to that added to the auxiliary reboiler, 13a.

The alcohol purification column 10 is operated at close to atmospheric pressure at the top. This column has about 15 to about 30 theoretical stages. The reflux ratio can be varied depending on whether wet or dry alcohol is desired in the bottoms. The reflux ratio can range from about 0.5/1 to about 3/1 by volume when it is desired to obtain alcohol with water contents of about 4 weight percent to about 2 weight percent respectively. A high reflux ratio is required to obtain essentially dry alcohol. To obtain alcohol containing about 0.2 weight percent weight water or less the reflux ratio is in the range of about 2.5/1 to about 6/1 by volume. In all cases reflux is taken from the entraining agent layer obtained from the decanter associated with this column.

Water washing of the entraining agent layer 17 in multi-stage counter-current extractor 20 should be accomplished at the lowest possible temperature to maximize the distribution of alcohol into water. At such temperatures (about 20°-45° C.) the ratio of water: entraining agent that is required can range from about 0.5:1 to about 1.5:1 by weight, the preferred range being about 0.5:1 to about 1:1. This column requires 3-10 theoretical stages.

Generally speaking, overall savings of about 25-30% are obtained when using the process of this invention as compared to efficient distillation systems and when equal proportions of dry and wet alcohol are to be produced.

In order to optimize the process of this invention to one with a minimum of energy requirements one must have heat exchange between all hot and cold streams. In the instant process this would necessitate installing heat exchangers between lines 1b and 8, 3 and 6, 6 and 11a, 15 and 19a, 15 and 24, 9a and 24, and 9 and 23 of the FIGURE.

If the crude aqueous solution of isopropyl alcohol to be treated by the method of this invention does not contain unknown oils, then the step of treating with activated carbon can be eliminated.

Although the invention has been described with a certain degree of particularity, it is understood that the present disclosure of the preferred forms has been made only by way of example and that numerous changes can be made without departing from the spirit and scope of the invention.

What is claimed is:

1. Process for separating $C_2$ to $C_4$ alkanols from an aqueous reaction solution containing low-boiling and high-boiling oils which comprises:
    (A) Contacting said aqueous solution with activated carbon whereby the high-boiling oils are removed;
    (B) Extracting the aqueous solution from (A) at about 75°-250° C. with at least one high boiling organic solvent selected from the group consisting of paraffins, napthenes, alkylated arenes, dialkylethers and aliphatic alcohols all having 12 to 25 carbons;
    (C) Cooling the extract from step (B) whereby an alkanol-water layer and a second extract layer are obtained and recycling said alkanol-water layer back to step (B);

(D) Distilling the second extract layer from (C) with an entraining agent selected from the group consisting of paraffins, naphthenes and dialkyl ethers, all having about 4 to about 12 carbon atoms, under superatmospheric pressure whereby a condensed vapor distillate comprising a mixture of alkanol, an entraining agent and water is obtained;

(E) Distilling the distillate of (D) under atmospheric pressure, employing the vapor in step (D) as a heat source into a purified alkanol bottoms product and a second distillate comprising a water-alkanol layer and an entraining agent layer;

(F) Returning part of the entraining agent from (E) to the distillation system of (E) and water washing the rest of the entraining agent to obtain:
  (i) a stream of entraining agent substantially free of alkanol, and
  (ii) an aqueous alkanol solution;
and
(G) Recycling the aqueous alkanol solution from steps (E) and (F) to the extracting step (B).

2. Method claimed in claim 1 wherein the paraffin used in step (B) is hexadecane.

3. Method claimed in claim 1 wherein the entraining agent used in step (D) is diisopropyl ether.

4. Method claimed in claim 1 wherein the extraction in step (B) is carried out at a temperature of about 100°–150° C.

5. Method claimed in claim 1 wherein the ratio of solvent: aqueous alkanol solution in step (B) is in the range of about 0.5:1 to about 8:1, by weight.

6. Method claimed in claim 1 wherein the distillation in step (D) is carried out under a pressure of about 50 to about 100 psig.

7. Method claimed in claim 1 wherein the alkanol is ethanol.

8. Method claimed in claim 1 wherein the alkanol is n-propanol.

9. Method claimed in claim 1 wherein the alkanol is n-butanol.

10. Method claimed in claim 1 wherein the alkanol is isobutanol.

11. Method claimed in claim 1 wherein the alkanol is 2-butanol.

12. Method claimed in claim 1 wherein the alkanol is 2-methyl-2-propanol.

13. Process for separating $C_2$ to $C_4$ alkanols from aqueous reaction solutions which comprises the steps of:

(A) Extracting the aqueous solution at about 75°–250° C. with at least one high boiling organic solvent selected from the group consisting of paraffins, naphthenes, alkylated arenes, dialkyl ethers and aliphatic alcohols all having 12 to 25 carbon atoms;

(B) Cooling the extract from step (A) whereby an alkanol-water layer and a second extract layer are obtained and recycling said alkanol-water layer back to step (A);

(C) Distilling the second extract layer from (B) with an entraining agent selected from the group consisting of paraffins, naphthenes and dialkyl ethers, all having about 4 to about 12 carbon atoms, under superatmospheric pressure whereby a condensed vapor distillate comprising a mixture of alkanol, an entraining agent and water is obtained;

(D) Distilling the distillate of (C) under atmospheric pressure, employing the vapor in step (C) as a heat source into a purified alkanol bottoms product and a second distillate comprising a water-alkanol layer and an entraining agent layer;

(E) Returning part of the entraining agent from (D) to the distillation system of (D) and water washing the rest of the entraining agent to obtain:
  (i) a stream of entraining agent substantially free of alkanol; and
  (ii) an aqueous alkanol solution; and
(F) Recycling the aqueous alkanol solution from steps (D) and (E) to the extracting step (A).

14. Method claimed in claim 1 wherein the alkanol is isopropanol.

* * * * *